United States Patent [19]

Biseniex et al.

[11] Patent Number: 4,485,239
[45] Date of Patent: Nov. 27, 1984

[54] 2-(2,6-DIMETHYL-3,5-DIETHOXYCARBONYL-1,4-DIHYDROPYRIDINE-4-CARBOXAMIDE GLUTARIC ACID ITS DISODIUM SALT AND METHOD OF THEIR PREPARATION

[75] Inventors: Egils A. Biseniex; Gunar Y. Dubur, both of Riga; Yan R. Uldrikis, Elgava; Maris M. Veveris; Agris A. Kimenis, both of Riga; Evgeny V. Ivanov, Leningrad, all of U.S.S.R.

[73] Assignee: Institut Organicheskogo Sinteza Akademii Nauk Latviiskoi SSR, Riga, U.S.S.R.

[21] Appl. No.: 536,899

[22] Filed: Sep. 28, 1983

[30] Foreign Application Priority Data

Oct. 25, 1982 [SU] U.S.S.R. .................. 3505378

[51] Int. Cl.³ .................. A61K 31/455; C07D 211/82
[52] U.S. Cl. .................. 546/321; 424/266
[58] Field of Search .................. 546/321; 424/266

[56] References Cited

U.S. PATENT DOCUMENTS 4,351,837  9/1982  Materne .................. 546/321

OTHER PUBLICATIONS

M. D. Mashkovsky, "Medicinal Preparations" (Manual Book on Pharmacotherapy for Physicians), Part I, 8th Edition, revised & supplemented, Moscow, Meditsina Publishers, 1977, pp. 370 to 373 (fragment) and Translation enclosed.

Primary Examiner—Henry R. Jiles
Assistant Examiner—Dale A. Bjorkman
Attorney, Agent, or Firm—Ladas & Parry

[57] ABSTRACT

2-(2,6-dimethyl-3,5-diethoxycarbonyl-1,4-dihydropyridine-4-carboxamide) glutaric acid of formula I and its disodium salt of formula II

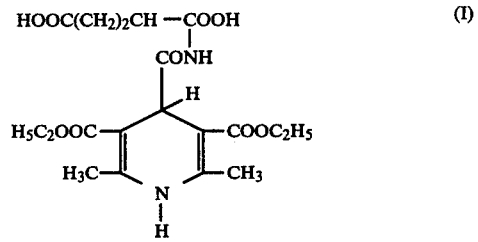

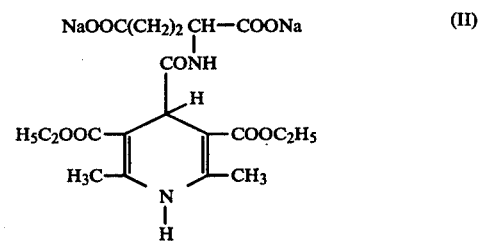

Said acid is obtained from glutaminic acid and dimethyl 3,5-diethoxycarbonyl-1,4-dihydroisonicotic acid.

For obtaining disodium salt, said acid is reacted with a caustic soda solution.

These compounds possess antiarrhythmic activity.

2 Claims, No Drawings

2-(2,6-DIMETHYL-3,5-DIETHOXYCARBONYL-1,4-DIHYDROPYRIDINE-4-CARBOXAMIDE GLUTARIC ACID ITS DISODIUM SALT AND METHOD OF THEIR PREPARATION

FIELD OF THE INVENTION

The present invention relates to organic synthesis and, more particularly, the invention relates to 2-(2,6-dimethyl-3,5-diethoxycarbonyl-1,4-dihydropyridine-4-carboxamide) glutaric acid, its disodium salt and to a method of preparation thereof. These compounds possess antiarrhythmic activity and may be used in medicine.

BACKGROUND OF THE INVENTION

Modern medical practice often has to deal with cardiac arrhythmia caused both by a pathologic heart state such as cardial ischemia, tachycardia and by various pharmaceutical prepartions, for example, strophanthin. In these cases preparations are used possesing antiarrhythmic activity, i.e. preparations curing the crdiac arythmia.

Antiarrhythmic activity is known to be displayed by quinidine and novocaine amide (procaine amide) (M.D.Mashkovsky, (Lekarstvennye sredstva" (Medicinal Agents), "Medicine" Publishers, Moscow, v.1, 1977, p.p. 370–372). However, these preparations are toxic and posses insufficient antiarrthythmic activity; cure the arrythmia in certain cases only and, furthermore, they cause some side-effects, e.g. drastically reduce the arterial pressure.

Preparations having pronounced antiarrhythmic activity within a wide range and causing no side-effects are not known in the present-day medical practice.

An object of the present invention is to provide a compound, which would possess a pronounced antiarrhythmic activity, cause no side-effects and be less toxic than the prior-art preparations.

BRIEF DESCRIPTION OF THE INVENTION

The above-mentioned object is attained by providing 2-(2,6-dimethyl-3,5-diethoxycarbonyl-1,4-dihydropyridine-4-carboxamide) glutaric acid, which, according to the invention, has formula I:

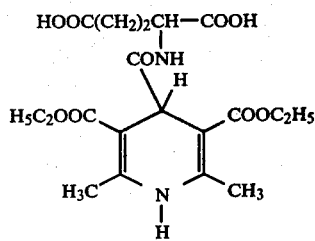

This compound is novel and consists of yellow odourless crystals, which are hardly soluble in water.

We have found that this compound posses pronouncedantiarrhythmic activity and may be used in medicine. However, it is preferable to use a disodium salt of 2-(2,6-dimethyl-3,5-diethoxycarbonyl-1,4-dihydropyridine-4-carboxamide) glutaric acid of formula II

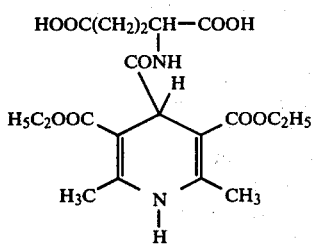

The disodium salt of formula II is also an odourless yellowish compound, but, in contrast to the above acid of formula I, this salt is well soluble in water. Therefore, it can be use both as a solution of injection and as tablets.

Compared to the known preparations—quinidine and novocaine amide (procaine amide)—the proposed disodium salt possess higher antiarrhythmic activity, wider pharmacologic activity, less toxic and causes no side effects.

An object of the present invention is a method of preparation of said compounds of formulas I and II.

Three versions of prreparation of 2-(2,6-dimethyl-3,5-diethoxycarbonyl-1,4-dihydropyridine-4-carboxamide) glutaric acid of formula I are proposed.

One version of preparation of the compound of formula I consists in that pentafluorophenyl ester of 2,6-dimethyl-3,5-diethoxycarbonyl-1,4-dihydroisonicotinic acid is reacted with glutamic acid in the presence of di-iso-propylethylamine in an inert organic solvent.

Another version of preparation of the compound of formula I includes a reaction of 2,6-dimethyl-3,5-diethoxycarbonyl-1,4-dihydrisonicotinic acid with glutamic acid and dicyclohexylcarbodiimide in the presence of 1-hydroxybenzotriazole in an inert organic solvent.

Another version of the method for preparation of the compound of formula I consists in that bis-trimethylsilyl ester of glutamic acid is reacted with mixed anhydride of 2,6-dimethyl-3,5-diethoxycarbonyl-1,4,-dihydropyridine-4-carboxylic acid and iso-butyl ester of carbonic acid at a temperature of 0° C. to −10° C. in an inert organic solvent.

The 2-(2,6-dimethyl-3,5-diethoxycarbonyl-1,4-dihydropyridine-4-carboxamide) glutaric acid obtained in the above embodiments of the present invention is reacted with caustic soda in an aqueous and organic medium to obtain the disodium salt of formula II.

The above-said initial components used in the claimed method are readily available substances or can easily be obtained from other components, which are also available. The initial glutamic acid is a commercial product produced in quantity. The initial 2.6-dimethyl-3,5-diethoxycarbonyl-1-4-dihydroisonicotinic acid can be produced from gluoxylic acid and β-aminocrotonic ester. Pentafluorophenyl ester of 2,6-dimethyl-3,5-diethoxycarbonyl-1,4-dihydroisonicotinic acid is produced by reacting 2,6-dimethyl-3,5-diethoxycarbonyl-1,4-dihydroisonicotinic acid with a pentafluorophenol and dicyclohexylcarbodiimide complex. The other initial components are well known and ordinarychemical reagents. The process of preparation of the product is effected under normal pressure and room (or slightly below room) temperature. Therefore, the proposed embodiments of the invention can easily be realized in industry.

DETAILED DESCRIPTION OF THE INVENTION

The action of 2-(2,6-dimethyl-3,5-diethoxycarbonyl-1,4-dihydropyridine-4-carboxamide) glutaric acid and its disodium salt on the cardiovascular system was studied in experiments with mice, rats, guinea pigs and cats. The antiarrhythmic activity and acute toxicity of the above compound have been studied. Antiarrhythmic agents such as quinidine and novocaine amide (procaine amide) were used for comparisons in the clinical study.

In the experiments on white mice narcotized with urethane ECGs were recorded in the second standard lead. A 2% solution of calcium chloride was injected into the tail vein at a constant rate (00.1 ml during 2 seconds). It has been found that preliminary administration (20–30 minutes prior to the narcosis) of the above compound considerably increases the arrhythmogenic and lethan doses of calcium chloride. The data is given in Table 1.

TABLE 1

Antagonism of investigated compounds towards the arrythmogenic and lethal effects of calcium chloride in experiments with mice

| Compound | Dose, mg/kg (interperitoneally) | Dose of CaCl$_2$, mg/kg arrhythmogenic | Lethal |
|---|---|---|---|
| Compound 1 | 3 | 98.4 | 105.0 |
| of formula II | 6 | 127.4 | 134.5 |
|  | 10 | 130.5 | 140.5 |
| Quinidine | 3 | 126.9 | 136.0 |
|  | 10 | 120.8 | 133.5 |
| Novocaine amide | 10 | 116.0 | 120.0 |
|  | 30 | 127.0 | 138.0 |
| Control | — | 85.0 | 100.0 |

From this Table it is clear that the compound of formula 1 features the same antiarrhythic effect as novocaine amide in a dose of 30 mg/kg.

Comparative study of the antiarrhythmic activity of the compounds on an aconitic model of arrhythmia was carried out on albino rats narcotized with urethane and chloralose (intraperitoneally), ECGs were recorded in the second standard lead. It has been found that said compound in case of its prrliminary intraperitoneal admisistration (30–40 minutes before the aconitine administration) exhibits a higher antiarrhythmic activity than quinidine and novocane amide. The data is given in Table 2.

TABLE 2

Antiarrhythmic activity and acute toxicity of investigated compounds

| Compound | ED$_{50}$, mg/kg Aconitic arrhythmia in rats | ED$_{50}$, mg/kg Strophanthin arrhythmia in guinea pigs | Acute toxicity in white mice upon intraperitonial administration LD$_{50}$* mg/kg |
|---|---|---|---|
| Compound of formula II | 3.0 ± 0.5 | 2.1 ± 0.3 | >2,000 |
| Quinidine | 4.3 ± 0.6 | 2.3 ± 0.4 | 156 (111.4–218.4) |
| Novocaine amide | 45.0 ± 5.0 | 55.0 ± 7.3 | 290 (145–580) |

*Confidence limit at P = 0.05.

It is clear from Table 2 that the average effective antiarrhythmic dose of the compound based on the aconitic model of arrhythmia is equl to 3.0 mg/kg, while that of novocaine amide is equala to 45 mg/kg.

Guinea pigs were narcotized with urethane and chloralose then strophanthin was administered in them, and against the background of arrhythmia, the above compound was administered intravenously. The doses of the compound, that arrest the strophanthin arrhythmia in the guinea pigs were recorded. From Table 2 it is clear that on this arrhythmia model, the compound II in its activity is not inferior to quinidine and considerably (approximately 25-fold) excels novocaine amide.

In acute experiments with cats narcotized with chloralose and urethane arterial pressure, respiration and ECG were recorded. The influence of the above comound on the arterial pressure, respiration, and on the haemodynamic effects of acetyl choline were investigated. Anaqueous solution of the compound was administered intravenously. It has been found that the compound in doses 0.1–0.2 g/kg does not cause any significant change in the arterial pressure, pulse rate and respiration rate; in doses of up to 4 mg/kg the compound does not reduce the response reaction to acetyl choline.

Acute toxicity was investigated on mongrel white mice of both sexes (Table 2). LD$_{50}$>2000 (intraperitonially), i.e. said compound is 1/12 as toxic as quinidine (LD$_{50}$=156 mg/kg).

On the basis of the data obtained we may state a number of advantages of the claimed compound over the quinidine and novocaine amide preparations used in clinical practice:

a higher activity on all kinds of experimental models of arrhythmia (calcium, aconitic and strophanthin ones);

a low toxicity (1/12 that of quinidine and 1/17 that of novocaine amide);

a wider range of therapeutic effects;

pronounced antiarrhythmic activity, both for preventing and for arresting experimental arrhythmias;

a stable effect on experimental strophanthin arrhythmia, which is very important in a clinic, because quinidine (the most effective present preparation for stopping strophanthin arrythmia) in some cases is ineffective;

a possibility of intravenous application not only due to water solubility and a high toxicity reserve but also due to the fact that the compound does not cause a drastic drop of the arterial pressure;

a possibility of using the compound per 0.5 (intragastric administration. i.e. in the from of tablets or powder)—both acid and salt may be used;

All this indicates to a possibility of practical utilization of 2-(2,6-dimethyl-3,5-diethoxycarbonyl-1,4-dihydropyridine-4-carboxamide) glutaric acid and its disodium salt in medicine for curing and arresting cardial arrhythmias. The invention is better understood with the following examples of obtaining 2-(2,6-dimethyl-3,5-diethoxycarbonyl-1,4-dihydropyridine-4-carbocamide) glutatic acid and its disodium salt.

EXAMPLE 1

Preparation of 2-(2,6-dimethyl-3,5-diethoxycarbonyl-1,4-dihydropyridine-4-carboxamide) glutaric acid.

First of all an initial substance—pentafluoro phenyl ester 2,6-dimethyl-3,5-diethoxycarbonyl-1.4-dihydroisonicotinic acid-is prepared. For this purpoe, added to a solution of 7.43 g (0.025 mole) 2,6-dimethyl-3,5-diethoxycarbonyl-1,4-dihydroisonicotinic acid in 50 ml of dimethylformamide (DMF) cooled to 0° C. are 28.8 g (0.038 mple) of complex "F" (complex "F" is a complex of pentafluorophenol and dicyclohexylcarbodiimide) in 30 ml of dimethylformamide. The mixture is stirred at room temperature for 48 hours. The precipitate of dicylohexalcarbamide is filtered out and the filtrate is evaporated in vacuum. The residue after the evaporation is crystallized from diethyl ester. The precipitate is filtered and dried in vacuum above KOH and $P_2O_5$.

The yield of pentafluoro phenyl ester of 2,6-dimethyl-3,5-diethoxycarbonyl-1,4-dihydroisonicotinic acid is 6.5 g (54.5%). M.p. 135° C.

Found, %: C 50.9; H 4.1; N 3.2.$C_{20}H_{18}NO_6F_5$.Calculated, %: C 51.8; H 3.9; N 3.0.

The PRM spectrum in dimethylsulphoxide (DMSO) $d_6\sigma$1.20 (6H, t., J=7.0Hz, $CH_3$-3.5-ester substituents), 2.28(6H, c., 2,6$CH_3$), 4.12 (4H q., J=7.0Hz, $Ch_2$- 3.5-ester substitutes), 5.04(1H, S4H), 21 ppm (1H S., NH).

Added to a solution of pentafluoro phenyl ester 2,6-dimethyl-3,5-diethyoxycarbonyl-1.4-dihydroisonicotinic acid in DMF cooled to 0° C. is 4.1 ml (0.024 mole) of di-iso-propylen amine and 2.1 g (0.014 mole) of powder-like glutaminic acid. The suspension is stirred for 48 hours at room temperature. The reaction mixture is evaporated in vacuum and the residue is dissolved in ethyl acetate and washed with 5% solution of $NaHSO_4$ and water. The ethyl acetate is evaporated, the residue is dried in vacuum and a yellowish fine-crystalline product is obtained.

The yield of 2-(2,6-dimethyl-3,5-diethoxycarbonyl-1,4-dihydropyridine-4-carboxamide) glutaric acid is 3.26 g (64%). M.p. 212° C.

Found, %: C 53.1; H 5.9; N 6.8 $C_{19}H_{26}N_2O_9$.
Calculated: C 53.5; H 6.2; N 6.6.

The PRM spectrum in DMSO - $d_6$, $\sigma$ 1.24 (6H, t. J=7.0 $CH_3$ - 3.5-ester substituents), 1.65-2.15 (4H m., —$CH_2CH_2$-2.22 (6H, s., 2.6 - $CH_3$), 3.95 (1H, m., $\alpha$ CH), 4.07 (4H, q., J=7.0 Hz, $CH_2$ - 3.5 - ester substituents), 4.36 (1H s, 4H) 6.90 (1H, d., J=8.0 Hz, CONH), 8.70 ppm (1H, s., NH).

EXAMPLE 2

Preparation of disodium salt of 2-(2,6-dimethyl-3,5-diethoxycarbonyl-1,4-dihydropyridine-4-carboxamide) glutaric acid.

Added to suspension of 2.98 g (0.007 mole) of 2-(2,6-dimethyl-3,5-diethoxycarbonyl-1,4-dihydropyridine-4-carboxamide) glutaric acid in 10 ml of water is 14 ml of 1N aqueous solution of NaOH (0.014 mole), the mixture being stirred continuously. The solution is evaporated in vacuum, and the residue is recrystallized from ethyl alcohol.

The yield of disodium salt of 2-(2,6-dimethyl-3,5-diethoxycarbonyl-1,4-dihydropyridine-4-carboxamide) glutaric acid is 2.8 g (86%). The melting point is 270° C. (with decomposition).

Found, % C 47.9; H 5.3; N 6.1. $C_{19}H_{24}N_2O_9Na_2$.
Calculated, %: C 48.5; H 5.1; N 6.0

The PMR spectrum in DMSO - $d_6$, $\sigma$: 1.20 (6H, t., J=7 Hz, $CH_3$- 3.5 - ester substituents), 1.65-1.85 (4H m., —$CH_2CH_2$—), 2.206 (6H, s., 2.6 - $CH_3$), 3.675 (1H, d., J=8.0 Hz, $\alpha$- CH), 4.07 (4H, q., J=7.0 Hz, $CH_2$ - 3.5 - ester substituents), 4.376 (1H, s., 4H), 7.066 (1H, d., J=6.2 Hz, COHN), 8.951 ppm (1H, s., NH).

EXAMPLE 3

Preparation of 2-(2,6-dimethyl-3,5diethoxycarbonyl-1,4-dihydropyridine-4-carboxamide) glutaric acid.

Added to a solution of 5.94 g (0.02 mole) of 2.6-dimethyl-3.5-diethoxycarbonyl-1,4-dihydroisonicotic acid in 50 ml dimethylformamide (DMF) at −5° C. are 4 g (0.01 mole) of dicyclohexylcarbodiimide in 15 ml of DMF and 2.7 g (0.020 mole) of 1-hydroxybenzotriazole, and the mixture is stirred at room temperature during 30 minutes. The precipitated dicyclohexyl urea is filtered off and 2.76 ml (0.02 mole) of triethylamine and 2.94 g (0.02 mole) of glutamic acid are added to the filtrate at −5° C. The reaction mixture is allowed to stand for 24 hours at 20° C., then it is evaporated in vacuum, and the residue is dissolved in ethyl acetate. The solution is washed with a 5% solution of $NaHS_4$ and with water. The ethyl acetate is evaporated and the residue is dried in vacuum.

3.2 g (37.6%) of 2-(2,6-dimethyl-3,5-diethoxycarbonyl-1,4-dihydropyridine-4-carboxamide) glutaric acid are obtained. M.p. 212° C.

EXAMPLE 4

Preparation of disodium salt of 2(2,6-dimethyl-3,5-diethoxycarbonyl-1,4-dihydropyridine-4-carboxamide) glutaric acid.

From 3.2 g of 2-(2,6-dimethyl-3,5-diethoxycarbonyl-1,4-dihydropyridine-4-carboxamide) glutaric acid following a procedure similar to that described in Example 2, 3.0 g (86%) of the desired product are obtained. M.p. 270° C. (with decomposition).

EXAMPLE 5

Preparation of 2-(2,6-dimethyl-3,5-diethoxycarbonyl-1,4-dihydropyridine-4-carboxamide) glutaric acid.

This example includes preparation of initial components: bis-trimethylsilyl ester of glutamic ester (solution A) and a mixed anhydride of 2,6-dimethyl-3,5-diethoxycarbonyl-1,4-dihydropyridine-4-carboxylic acid and iso-butyl ester of carbonic acid (solution B).

(1) Preparation of bis-triethylsilyl ester of glutamic acid (solution A).

Added to 1.47 g (0.01 mole) of glutamic acid in 15 ml chloroform are 3.2 g (0.02 mole) of hexamethyldisilasane and 50 ml of concentrated sulphuric acid. The formation of bis-trimethyl ester of glutamic acid in the form of a transparent solution is completed within 45 minutes at 50-60° C.

(2) Preparation of mixed ahydride of 2,6dimethyl-3,5-diethoxycarbonyl-1,4-dihydropyridine-4-carboxylic acid and isobutyl ester of carbonic acid (solution B).

To a suspension of 2.97 g (0.01 mole) of 2,6-dimethyl-3,5-diethoxycarbonyl-1,4-dihydroisonicotinic acid in 20 ml of chloroform, cooled down to -20° C., 1,37 g (0.01 mole) l of isobutyl ester of chlorocarbonic acid and 1.0 g (0.01 mole) of triethylamine are added. The mixture is stirred at −10° C. for 1 hour, and the resulting mixed anhydride without isolation is used in the subsequent reactions.

Solution A is added to solution B containing the mixed anydride, the procedure being effected at −10° C. with stirring. The resulting solution is stirred for 1 hour at −10° C., kept at room temperature for 24 hours washed three times with 40 ml of water, filtered and dried over anhydrous $Na_2SO_4$. The solvent is evaporated in vacuum, the residue is dried in a vacuum dyring cabinet at 20 mm Hg and 40° C. for 10 hours. 1.5 g (35.2%) of a light yellow crystalline powder were thus obtained. M.p. 212° C.

EXAMPLE 6

Preparation of disodium salt of 2-(2,6-dimethyl-3,5-diethoxycarbonyl-1,4-dihydropyridine-4-carboxamide) glutaric acid.

From 1.5 of (2.6-dimethyl-3,5-diethoxycarbonyl-1,4-dihydropyridine-4-carboxamide) glutaric acid, following a procedure similar to that described in Example 2, 1.41 g (86%) of the desired product are obtained. M.p. 270° C. (with decomposition).

We claim:

1. 2-(2,6-dimethyl-3,5-diethoxycarbonyl-1,4-dihydropyridine-4-carboxamide) glutaric acid of formula I

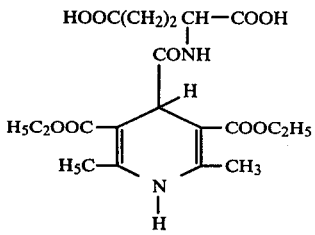

2. A disodium salt of 2-(2,6-dimethyl-3,5-diethoxycarbonyl 1-1,4-dihydropyridine-4-carboxamide) glutaric acid according to claim 1, which has formula II

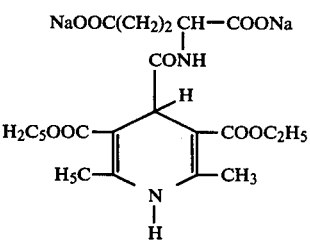

* * * * *